United States Patent
Von Oepen

(10) Patent No.: US 8,556,511 B2
(45) Date of Patent: Oct. 15, 2013

(54) FLUID BEARING TO SUPPORT STENT TUBING DURING LASER CUTTING

(75) Inventor: Randolf Von Oepen, Los Altos, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 502 days.

(21) Appl. No.: 12/877,600

(22) Filed: Sep. 8, 2010

(65) Prior Publication Data

US 2012/0057813 A1 Mar. 8, 2012

(51) Int. Cl.
*F16C 32/06* (2006.01)

(52) U.S. Cl.
USPC .......................................... 384/114; 384/901

(58) Field of Classification Search
USPC ..................... 384/100, 114, 901; 219/121.72
See application file for complete search history.

(56) References Cited

U.S. PATENT DOCUMENTS

| | | | |
|---|---|---|---|
| 3,471,125 A | * | 10/1969 | Fleer et al. .................. 415/112 |
| 3,639,074 A | * | 2/1972 | Killick ........................ 415/110 |
| 3,802,306 A | | 4/1974 | Brown et al. |
| 4,387,952 A | | 6/1983 | Slusher |
| 4,474,468 A | | 10/1984 | Shirakura et al. |
| 4,694,139 A | | 9/1987 | Roder |
| 4,729,766 A | | 3/1988 | Bergentz et al. |
| 4,733,665 A | | 3/1988 | Palmaz |
| 4,736,381 A | | 4/1988 | Eden et al. |
| 4,862,886 A | | 9/1989 | Clarke et al. |
| 4,893,972 A | | 1/1990 | Blaho |
| 4,947,022 A | | 8/1990 | Ostroff et al. |
| 4,963,022 A | | 10/1990 | Sommargren |
| 4,994,071 A | | 2/1991 | MacGregor |
| 5,049,723 A | | 9/1991 | MacDonald et al. |
| 5,059,211 A | | 10/1991 | Stack et al. |
| 5,064,537 A | | 11/1991 | Chupka et al. |
| 5,073,694 A | | 12/1991 | Tessier et al. |
| 5,102,417 A | | 4/1992 | Palmaz |
| 5,160,823 A | | 11/1992 | Bennin et al. |
| 5,169,678 A | | 12/1992 | Cole et al. |
| 5,222,617 A | | 6/1993 | Gregory et al. |
| 5,243,615 A | | 9/1993 | Ortiz et al. |
| 5,306,286 A | | 4/1994 | Stack et al. |
| 5,345,057 A | | 9/1994 | Muller |
| 5,356,423 A | | 10/1994 | Tihon et al. |

(Continued)

FOREIGN PATENT DOCUMENTS

EP    0 221 570 A2    5/1987
EP    0 364 787 A1    4/1990

(Continued)

OTHER PUBLICATIONS

C.H. Fan et al., "Plasma Absorption of Femtosecond Laser Pulses in Dielectrics," Journal of Heat Transfer, Apr. 2002, vol. 124, pp. 275-283.

(Continued)

*Primary Examiner* — James Pilkington
(74) *Attorney, Agent, or Firm* — Fulwider Patton LLP

(57) ABSTRACT

A fluid bearing assembly provides support to stent tubing while the stent tubing is undergoing laser cutting to form a stent pattern. The fluid bearing assembly supports the stent tubing and provides a fluid barrier between the bearing and the stent tubing thereby providing nearly frictionless movement between the support bearing and the stent tubing.

34 Claims, 3 Drawing Sheets

(56) References Cited

U.S. PATENT DOCUMENTS

| | | |
|---|---|---|
| 5,406,410 A | 4/1995 | Hanna et al. |
| 5,421,955 A | 6/1995 | Lau et al. |
| 5,514,154 A | 5/1996 | Lau et al. |
| 5,521,374 A | 5/1996 | Cray et al. |
| 5,569,295 A | 10/1996 | Lam |
| 5,591,197 A | 1/1997 | Orth et al. |
| 5,603,722 A | 2/1997 | Phan et al. |
| 5,605,696 A | 2/1997 | Eury et al. |
| 5,611,946 A | 3/1997 | Leong et al. |
| 5,656,186 A | 8/1997 | Mourou et al. |
| 5,701,319 A | 12/1997 | Fermann |
| 5,720,894 A | 2/1998 | Neev et al. |
| 5,759,192 A | 6/1998 | Saunders |
| 5,780,807 A | 7/1998 | Saunders |
| 5,807,404 A | 9/1998 | Richter |
| 5,824,049 A | 10/1998 | Ragheb et al. |
| 5,854,805 A | 12/1998 | Reid et al. |
| 5,909,306 A | 6/1999 | Goldberg et al. |
| 5,928,280 A | 7/1999 | Hansen et al. |
| 5,948,596 A | 9/1999 | Zhong et al. |
| 5,968,088 A | 10/1999 | Hansen et al. |
| 6,001,123 A | 12/1999 | Lau |
| 6,017,362 A | 1/2000 | Lau |
| 6,131,266 A | 10/2000 | Saunders |
| 6,132,461 A | 10/2000 | Thompson |
| 6,156,030 A | 12/2000 | Neev |
| 6,160,240 A | 12/2000 | Momma et al. |
| 6,163,010 A | 12/2000 | Kobsa |
| 6,183,506 B1 | 2/2001 | Penn et al. |
| 6,197,047 B1 | 3/2001 | Kranz |
| 6,208,458 B1 | 3/2001 | Galvanauskas et al. |
| 6,214,115 B1 | 4/2001 | Taylor et al. |
| 6,217,608 B1 | 4/2001 | Penn et al. |
| 6,229,829 B1 | 5/2001 | Yin |
| 6,231,598 B1 | 5/2001 | Berry et al. |
| 6,241,762 B1 | 6/2001 | Shanley |
| 6,245,101 B1 | 6/2001 | Drasler et al. |
| 6,245,103 B1 | 6/2001 | Stinson |
| 6,248,129 B1 | 6/2001 | Froix |
| 6,254,632 B1 | 7/2001 | Wu et al. |
| 6,273,911 B1 | 8/2001 | Cox et al. |
| 6,281,262 B1 | 8/2001 | Shikinami |
| 6,281,471 B1 | 8/2001 | Smart |
| 6,287,335 B1 | 9/2001 | Drasler et al. |
| 6,287,336 B1 | 9/2001 | Globerman et al. |
| 6,293,967 B1 | 9/2001 | Shanley |
| 6,312,460 B2 | 11/2001 | Drasler et al. |
| 6,324,195 B1 | 11/2001 | Suzuki et al. |
| RE37,585 E | 3/2002 | Mourou et al. |
| 6,368,052 B2 * | 4/2002 | Uesugi et al. .................. 415/80 |
| 6,369,355 B1 | 4/2002 | Saunders |
| 6,375,677 B1 | 4/2002 | Penn et al. |
| 6,395,326 B1 | 5/2002 | Castro et al. |
| 6,411,636 B1 | 6/2002 | Ota et al. |
| 6,419,693 B1 | 7/2002 | Fariabi |
| 6,423,085 B1 | 7/2002 | Murayama et al. |
| 6,423,092 B2 | 7/2002 | Datta et al. |
| 6,451,051 B2 | 9/2002 | Drasler et al. |
| 6,463,314 B1 | 10/2002 | Haruna |
| 6,464,720 B2 | 10/2002 | Boatman et al. |
| 6,468,302 B2 | 10/2002 | Cox et al. |
| 6,475,138 B1 | 11/2002 | Schechter et al. |
| 6,475,237 B2 | 11/2002 | Drasler et al. |
| 6,482,166 B1 | 11/2002 | Fariabi |
| 6,489,589 B1 | 12/2002 | Alexander |
| 6,492,615 B1 | 12/2002 | Flanagan |
| 6,511,505 B2 | 1/2003 | Cox et al. |
| 6,517,888 B1 | 2/2003 | Weber |
| 6,517,889 B1 | 2/2003 | Jayaraman |
| 6,521,865 B1 | 2/2003 | Jones et al. |
| 6,527,799 B2 | 3/2003 | Shanley |
| 6,531,679 B2 | 3/2003 | Heerman et al. |
| 6,537,480 B1 | 3/2003 | Becker et al. |
| 6,558,733 B1 | 5/2003 | Hossainy et al. |
| 6,562,065 B1 | 5/2003 | Shanley |
| 6,563,080 B2 | 5/2003 | Shapovalov et al. |
| 6,572,647 B1 | 6/2003 | Supper et al. |
| 6,602,284 B2 | 8/2003 | Cox et al. |
| 6,626,939 B1 | 9/2003 | Burnside et al. |
| 6,629,994 B2 | 10/2003 | Gomez et al. |
| 6,641,607 B1 | 11/2003 | Hossainy et al. |
| 6,653,426 B2 | 11/2003 | Alvarado et al. |
| 6,676,697 B1 | 1/2004 | Richter |
| 6,690,511 B2 | 2/2004 | Engelhardt et al. |
| 6,719,934 B2 | 4/2004 | Stinson |
| 6,734,387 B2 | 5/2004 | Kafka et al. |
| 6,736,843 B1 | 5/2004 | Fariabi |
| 6,758,860 B1 | 7/2004 | Penn et al. |
| 6,770,089 B1 | 8/2004 | Hong et al. |
| 6,796,997 B1 | 9/2004 | Penn et al. |
| 6,827,734 B2 | 12/2004 | Fariabi |
| 6,852,124 B2 | 2/2005 | Cox et al. |
| 6,858,037 B2 | 2/2005 | Penn et al. |
| 6,869,212 B2 * | 3/2005 | Uesugi et al. .................. 384/113 |
| 6,878,162 B2 | 4/2005 | Bales et al. |
| 6,878,901 B2 | 4/2005 | Johnson et al. |
| 6,881,223 B2 | 4/2005 | Penn et al. |
| 6,887,264 B2 | 5/2005 | Penn et al. |
| 6,927,359 B2 | 8/2005 | Kleine et al. |
| 7,044,963 B1 | 5/2006 | Richter |
| 7,077,859 B2 | 7/2006 | Sirhan et al. |
| 7,094,255 B2 | 8/2006 | Penn et al. |
| 7,160,321 B2 | 1/2007 | Shanley |
| 7,169,140 B1 | 1/2007 | Kume |
| 7,175,734 B2 | 2/2007 | Stewart et al. |
| 7,179,288 B2 | 2/2007 | Shanley |
| 7,258,697 B1 | 8/2007 | Cox et al. |
| 7,279,004 B2 | 10/2007 | Shanley |
| 7,294,146 B2 | 11/2007 | Chew et al. |
| 7,326,244 B2 | 2/2008 | Drasler et al. |
| 7,534,257 B2 | 5/2009 | Richter |
| 2002/0082679 A1 | 6/2002 | Sirhan et al. |
| 2002/0082685 A1 | 6/2002 | Sirhan et al. |
| 2002/0198589 A1 | 12/2002 | Leong |
| 2003/0050692 A1 | 3/2003 | Sirhan et al. |
| 2003/0052101 A1 | 3/2003 | Gu et al. |
| 2003/0081192 A1 | 5/2003 | Nishi |
| 2003/0139801 A1 | 7/2003 | Sirhan et al. |
| 2004/0059408 A1 | 3/2004 | Alvarado et al. |
| 2004/0127970 A1 | 7/2004 | Saunders et al. |
| 2004/0226922 A1 | 11/2004 | Flanagan |
| 2004/0230290 A1 | 11/2004 | Weber et al. |
| 2005/0033412 A1 | 2/2005 | Wu et al. |
| 2005/0070996 A1 | 3/2005 | Dinh et al. |
| 2005/0087520 A1 | 4/2005 | Wang et al. |
| 2006/0033240 A1 | 2/2006 | Weber et al. |
| 2006/0041102 A1 | 2/2006 | Hossainy et al. |
| 2006/0054604 A1 | 3/2006 | Saunders |
| 2006/0207977 A1 | 9/2006 | Hermann et al. |
| 2007/0151961 A1 | 7/2007 | Kleine et al. |
| 2008/0269870 A1 | 10/2008 | Ruuttu et al. |

FOREIGN PATENT DOCUMENTS

| | | |
|---|---|---|
| EP | 0 372 789 A3 | 6/1990 |
| EP | 0 421 729 A2 | 4/1991 |
| EP | 0 540 290 A2 | 5/1993 |
| EP | 0 541 443 A1 | 5/1993 |
| EP | 0 562 150 A1 | 9/1993 |
| EP | 0 624 421 A2 | 11/1994 |
| EP | 0 662 307 A1 | 7/1995 |
| EP | 0 679 373 A2 | 11/1995 |
| EP | 0 714 641 A2 | 6/1996 |
| EP | 0815804 A1 | 7/1998 |
| EP | 1 466 634 A1 | 10/2004 |
| GB | 2 070 490 A | 9/1981 |
| GB | 2239733 A | 10/1991 |
| JP | 61169188 | 7/1986 |
| JP | Heisei 5-285898 | 11/1993 |
| JP | 09108880 A | 4/1997 |
| WO | 92/06734 | 4/1992 |
| WO | 0013839 | 3/2000 |

(56) References Cited

FOREIGN PATENT DOCUMENTS

OTHER PUBLICATIONS

Brochure: Industrial Strength Laser Marking: Turning Photons into Dollars, printed by Excel/Control Laser, Inc., 1992.

Brochure: Anomatic TM II Positioning Controller, printed by Anorad Corporation (undated).

J.Sun et al., "Inert gas beam delivery for ultrafast laser micromachining at ambient pressure," Journal of Applied Physics, Jun. 13, 2001, vol. 89, No. 12, pp. 8219-8224.

International Search Report dated Jul. 21, 2010.

* cited by examiner

FLUID BEARING TO SUPPORT STENT TUBING DURING LASER CUTTING

BACKGROUND OF THE INVENTION

The invention relates generally to improvements in the manufacture of expandable stents and, more particularly, to new and improved methods and apparatus for direct laser cutting of stents in providing stents of enhanced structural quality.

Stents are expandable endoprosthesis devices which are adapted to be implanted into a patient's body lumen, such as a blood vessel or coronary artery, to maintain the patency of the artery. These devices are typically used in the treatment of atherosclerotic stenosis in blood vessels, coronary arteries, and the like.

In the medical arts, stents are generally tubular-shaped devices which function to hold open a segment of a blood vessel or other anatomical lumen. Stents are very high precision, relatively fragile devices and, ideally, the most desirable stents incorporate a very fine precision structure cut from a very small diameter, thin-walled cylindrical tube. In this regard, it is extremely important to make precisely dimensioned, smooth, narrow cuts in the thin-walled tubing in extremely fine geometries without damaging the narrow struts that make up the stent structure. Prior art stents typically are cut by a laser and held by collet in a computer controlled machine that translates and rotates the stent as the laser cuts through the outer surface of the metal tubing. In order to stabilize the stent tubing, typically a bushing surrounds the stent tubing and is positioned between the laser and the collet holding the stent. Prior art bearings or bushings create a small amount of friction between the stent tubing and the bearing which can cause slight imperfections in the laser cutting process as the stent tubing is moved relative to the bearing.

Referring to FIGS. 1-3, a typical prior art laser assembly is shown in which a laser beam is used to cut a pattern in stent tubing. The stent tubing is mounted in the collet of a CNC controller which will move the stent tubing in a translational and rotational direction while the laser beam cuts through one wall of the stent tubing to form a pattern. As shown, a bushing is used to support the stent tubing between the collet and the laser beam (or proximal to the laser beam). The prior art bushings typically support the stent tubing, however, because the inner diameter of the support bushing is closely matched to the outer diameter of the stent tubing, there is some amount of drag or friction between the bushing and the stent tubing. The control system must supply sufficient force to overcome the inertia of the tubing and the drag caused by the interface between the bushing and the stent tubing, and at the same time accurately position the stent tubing for laser cutting. It is therefore a goal to reduce cutting errors due to sticking and choppiness in the movement of the stent tubing and to improve yields.

Accordingly, the manufacturers of stents have long recognized the need for improved manufacturing processes and to reduce the amount of friction between the bearing and the stent tubing during the laser cutting process. The present invention fulfills these needs.

SUMMARY OF THE INVENTION

In general terms, the present invention provides a new and improved method and apparatus for direct laser cutting stents by enabling greater precision, reliability, structural integrity and overall quality.

The present invention provides an improved system for producing stents with a fine precision structure cut from a small diameter, thin-walled, cylindrical tube. The tubes are typically made of stainless steel, other biocompatible materials, or biodegradable materials, and are fixtured under a laser and positioned utilizing a CNC machine to generate a very intricate and precise pattern. Due to the thin wall and the small geometry of the stent pattern, it is necessary to have very precise control of the laser, its power level, the focus spot size, and, importantly, the precise positioning of the laser cutting path.

In keeping with the invention, a stent tubing is held in a collet in a CNC machine so that the stent tubing is able to rotate and translate relative to a fixed laser beam. In order to support the stent tubing, a bearing or bushing supports the stent tubing just proximal to the laser beam (between the collet and the laser beam). In this manner, the stent tubing is prevented from sagging or deflecting away from the laser beam, which would otherwise create inaccuracies in the cut stent pattern. In the present invention, a fluid bearing includes a housing having a gas inlet port and a fluid inlet port on its outer surface. A bearing is positioned within the housing and the bearing has multiple blades that are aligned with the gas inlet port on the housing. The bearing is free to rotate within the housing without touching the housing. The gas inlet port is positioned to inject a high pressure gas on the blades in order to impart a high speed rotation of the bearing within the housing. The fluid inlet port on the housing is positioned to inject fluid onto an inner surface of the bearing so that as the bearing rotates at high speed, a thin film of fluid adheres to the inner surface of the bearing. The stent tubing is inserted through an inner diameter of the bearing so that the bearing supports the stent tubing just proximal of the laser beam. As the bearing rotates at high speed, on the order of about 1,000 to 10,000 rpm (or higher), the film of fluid adheres to the inner surface of the bearing so that the film of fluid is between the inner surface of the bearing and the outer surface of the stent tubing. Since the bearing is rotating at high speed and a film of fluid is formed between the inner surface of the bearing and the outer surface of the stent tubing, the stent tubing is centered within the bearing thereby creating a near frictionless environment as the stent tubing translates and rotates relative to the laser beam. The fluid film has very low friction and will not place a significant resistive load on the stent tubing as the collet or CNC system rotates and translates the stent tubing relative to the laser beam.

The advantages of the present invention will be apparent from the following more detailed description when taken in conjunction with the accompanying drawings of exemplary embodiments.

DETAILED DESCRIPTION OF THE PREFERRED EMBODIMENTS

Figure 1:
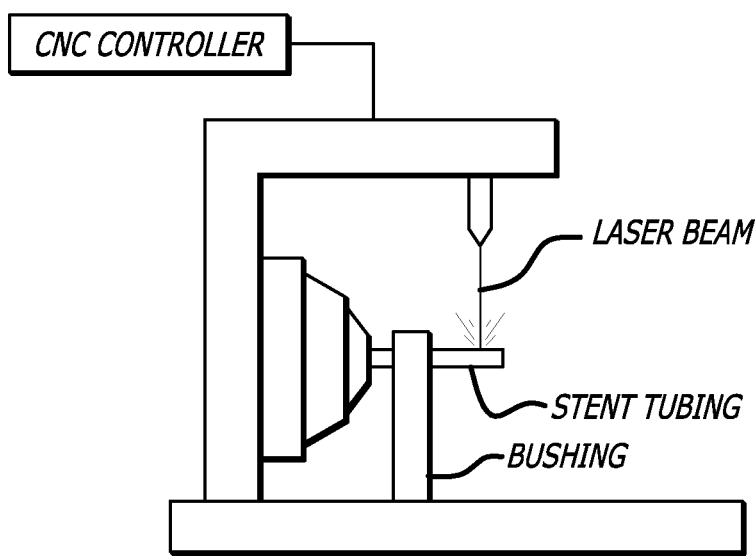
FIG. 1 is a plan view depicting a prior art laser cutting assembly for cutting a pattern in stent tubing.
Figure 2:
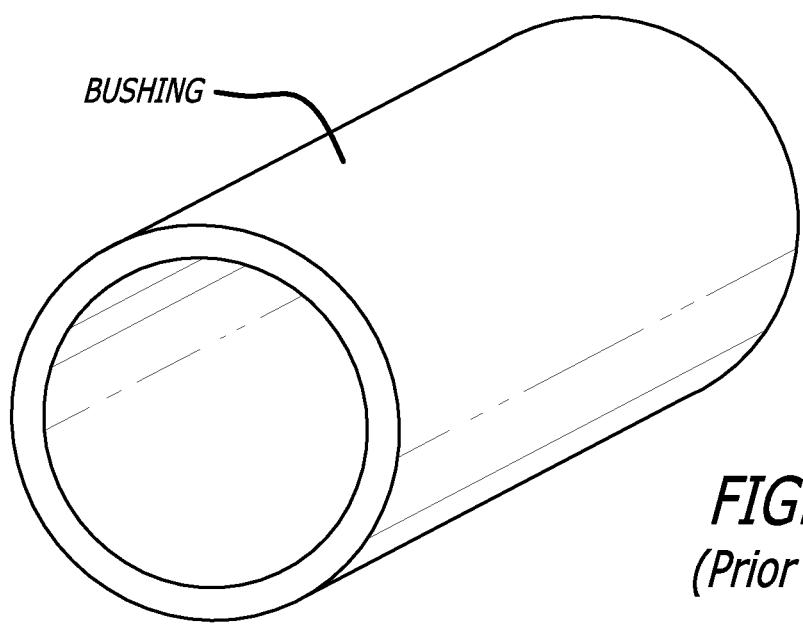
FIG. 2 is a perspective view of a prior art bushing used to support stent tubing during a laser cutting operation.
Figure 3:
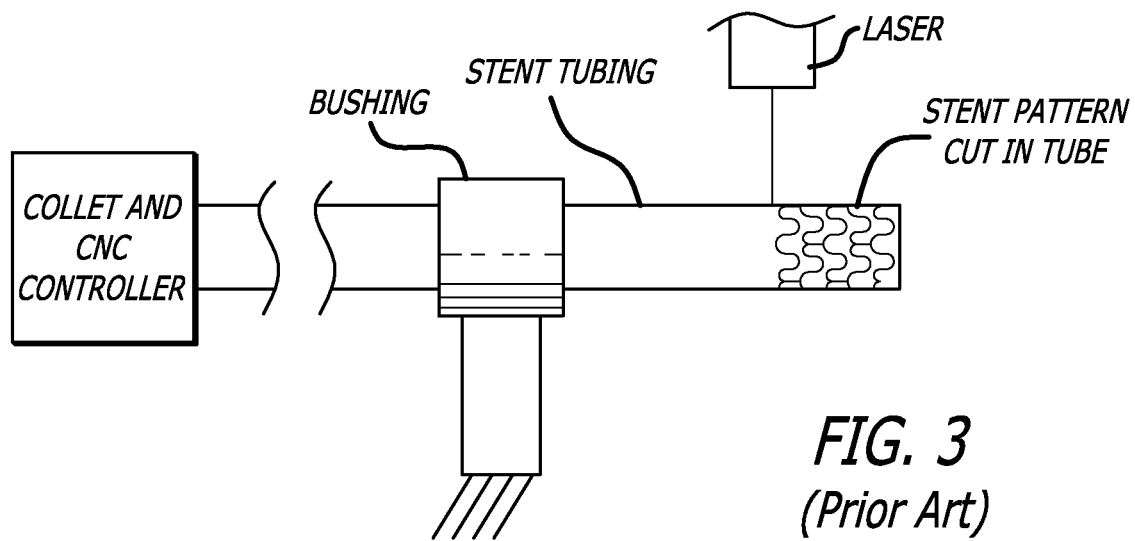
FIG. 3 is a partial elevational view of a prior art laser cutting assembly in which a bushing receives the stent tubing for support during a laser cutting process.
Figure 4:
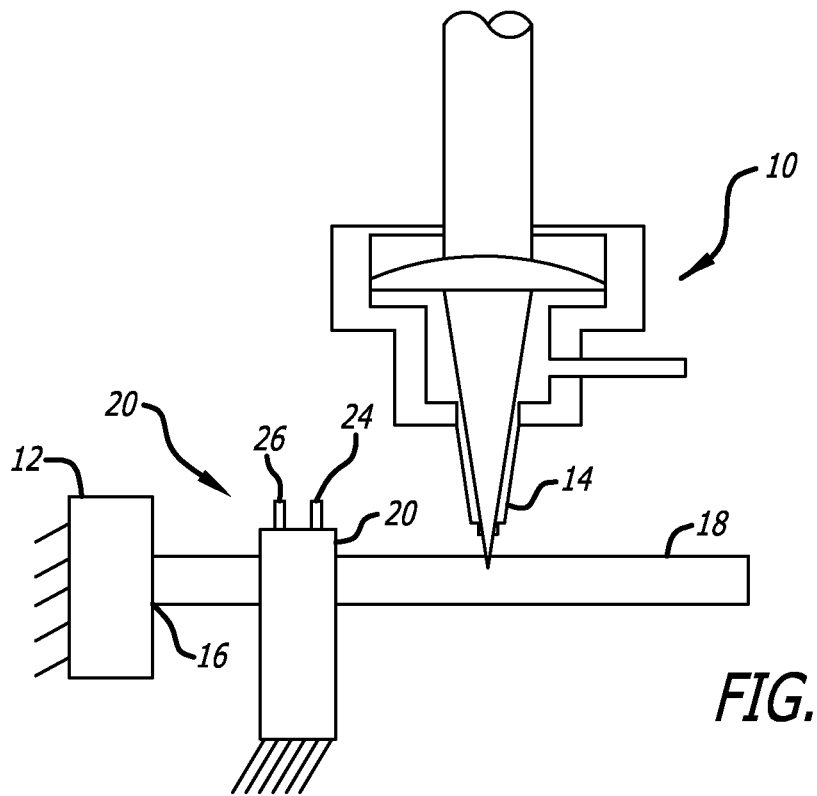
FIG. 4 is a plan view of a laser cutting assembly in which a fluid bearing is used to support stent tubing during a laser cutting process.
Figure 5:
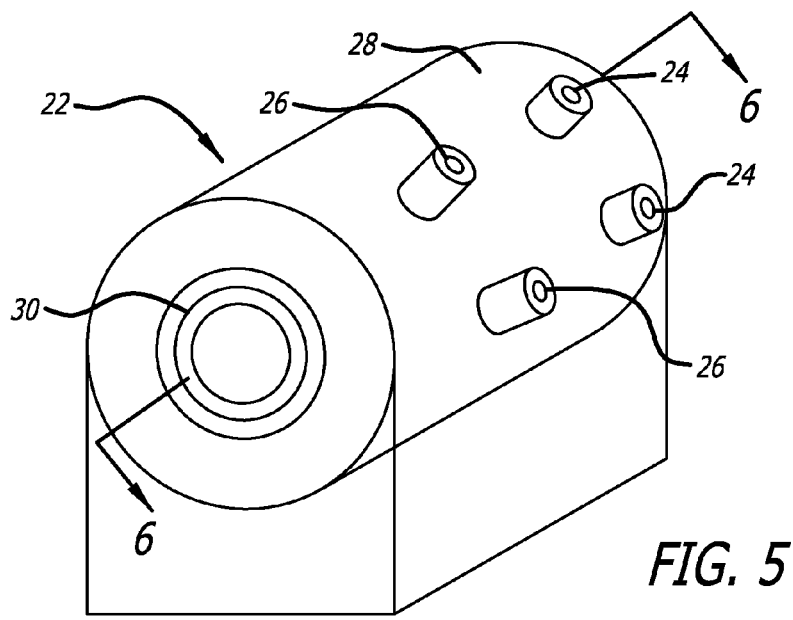
FIG. 5 is a perspective view depicting a fluid bearing assembly for use in supporting stent tubing during a laser cutting process.
Figure 6:
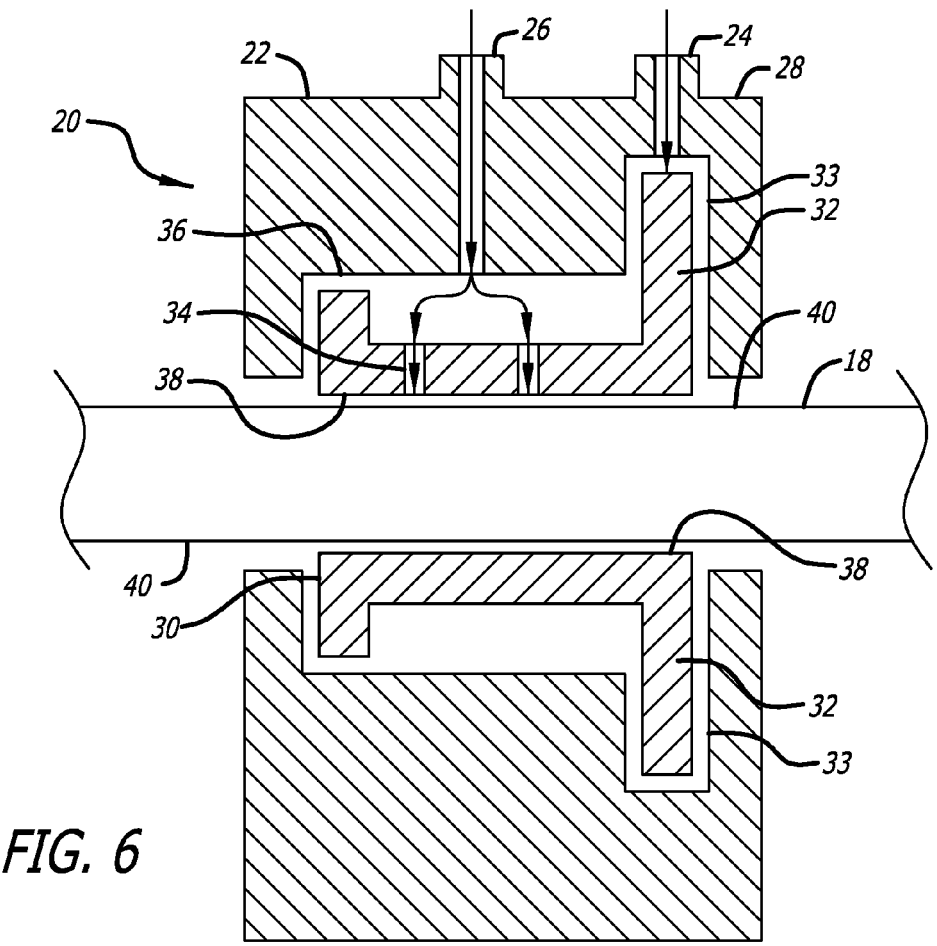
FIG. 6 is a partial cross-sectional view depicting a fluid bearing for supporting stent tubing during a laser cutting process.

In keeping with the present invention, as shown in FIGS. 4-6, a laser cutting assembly 10 includes a CNC controller 12 and a laser beam assembly 14. The laser beam assembly is well known in the art and includes numerous components such as a focusing lens, coaxial gas jet, and the laser beam itself. The laser cutting assembly 10 also includes a collet 16, which is well known in the art, and is used for the purpose of holding a stent tubing 18 and moving the stent tubing in a translational and rotational direction. The stent tubing 18 is mounted in the collet 16 and the stent tubing extends away from the collet so that it is positioned directly under the laser beam assembly 14. Typically, the laser beam assembly, and the laser beam itself, remain stationary during the stent cutting process, while the stent tubing translates and rotates while the laser beam removes material from the tubing.

In further keeping with the invention, a fluid bearing 20 is provided to support the stent tubing 18. More specifically, the fluid bearing includes a housing 22 that will be anchored at one end so that the housing is stationary and firmly supports the stent tubing. The housing has a gas inlet port 24 and a fluid inlet port 26 on its outer surface 28. Depending upon the specific requirements, more than one gas inlet port 24 and fluid inlet port 26 can be provided and spaced along the outer surface 28 of the housing 22. Typically, the multiple gas inlet ports or fluid inlet ports would extend in alignment circumferentially around the outer surface 28 of the housing 22. A bearing 30 is contained within the housing 22 so that the bearing can rotate at high speed within the housing without hitting or touching the walls of the housing. The bearing 30 has one or more blades 32 that are positioned in grooves 33 in the housing 22 which align with the gas inlet port 24. When high pressure gas is injected into gas inlet port 24, the gas will impinge on the blades 32 thereby causing the bearing 30 to rotate at high speeds. For example, it is contemplated that the bearing 30 will rotate at speeds between 1,000 rpm up to 10,000 rpm. In another embodiment, it may be appropriate for the bearing 30 to rotate at speeds between 10,000 rpm up to 100,000 rpm.

With reference in particular to FIG. 6, the bearing 30 has one or more fluid channels 34 that will allow fluid to pass from the fluid inlet port 26 into a cavity 36 and through the fluid channels 34 onto the inner surface 38 of the bearing 30.

In use, the present invention provides a low friction fluid film between the bearing and the stent tubing so that the amount of friction between the bearing and the stent tubing is substantially reduced from the prior art devices. Again, referring to FIGS. 4-6, a fluid is injected through fluid inlet port 26 on the housing 22 and a high pressure gas is injected through gas inlet port 24, also on housing 22. The high pressure gas impinges on the blades 32 which cause the bearing 30 to rotate at a high speed as previously disclosed. As the bearing 30 rotates at high speed, the fluid is forced from the fluid inlet port into cavity 36 where it can flow through fluid channels 34 in the bearing 30 and onto the inner surface of the bearing 38. As the bearing 30 rotates at high speeds, the shear between the bearing and the fluid will cause a film of fluid to adhere to the bearing inner surface 38 and this film will separate the outer surface 40 of the stent tubing 18 from the bearing 30. The fluid film has a very low coefficient of friction, and accordingly will not place a significant resistive load on the stent tubing as the collet 16 attempts to rotate and translate the stent tubing relative to the laser beam. Further, the high rotational speeds of the bearing 30, in conjunction with the film fluid that adheres to the inner surface 38 of the bearing, act to center the stent tubing 18 relative to the bearing 30. This further allows the laser beam to precisely cut the stent pattern so that a more accurate stent pattern can be reproducably manufactured.

In one embodiment, the space between the blades 32 and the grooves 33 in the housing 22 may be sufficient to allow the high pressure gas to be directed toward the stent tubing. This serves several purposes including allowing the gas to exhaust from the bearing 30, thereby allowing more gas to be injected to drive the bearing rotation. Further, as the gas exhausts, it may exert a pressure in the direction opposite to the flow of fluid along the stent tubing thereby forcing fluid out of the space between the bearing 30 and the stent tubing 18 in only one direction. This will prevent contamination of the region opposite to the exit location, namely where the laser is cutting the pattern in the stent tubing.

In an alternative embodiment, the blades 32 may be either flat fins or have a tilted configuration such as the blades found in a turbine (not shown). In either configuration, the grooves 33 that receive the blades 32 will be configured to accommodate the blades as the bearing 30 rotates. Further, the blades also can have a curved configuration and still provide the rotational forces on the bearing as described. In one embodiment, the blades have a rectangular shape and are substantially flat fins.

The fluid used with the present invention can be water, saline or any thin oil such as a mineral oil. Further, the high pressure gas typically will be air.

The housing 22 can be formed from any rigid material such as stainless steel, while the bearing 30 is formed from a low friction material such as a polymer, including such polymers such as PTFE.

It will be apparent from the foregoing that the present invention provides a new and improved method and apparatus for laser cutting stents thereby enabling greater precision, reliability and overall quality in forming precise stent patterns in stent tubing. Other modifications and improvements may be made without departing from the scope of the invention. Accordingly, it is not intended that the invention be limited, except by the appended claims.

What is claimed:

1. A fluid bearing assembly, comprising:
   a housing having a gas inlet port and a fluid inlet port;
   a bearing having a plurality of blades and being rotably mounted within the housing so that the bearing is free to rotate without touching the housing;
   the gas inlet port being positioned to inject pressurized gas on the plurality of blades to impart rotation to the bearing; and
   the fluid inlet port being positioned to inject fluid onto an inner surface of the bearing so that as the bearing rotates, a film of fluid adheres to the inner surface of the bearing.

2. The fluid bearing assembly of claim 1, wherein a plurality of gas inlet ports are positioned to inject the pressurized gas on the blades of the bearing.

3. The fluid bearing assembly of claim 2, wherein the gas inlet ports are positioned on an outer surface of the housing.

4. The fluid bearing assembly of claim 1, wherein a plurality of fluid inlet ports are positioned on an outer surface of the housing.

5. The fluid bearing assembly of claim 4, wherein the plurality of fluid injection ports are spaced apart in alignment around a circumference of the housing.

6. The fluid bearing assembly of claim 1, wherein the fluid injection port is in fluid communication with a cavity formed by an inner surface of the housing and an outer surface of the bearing.

7. The fluid bearing assembly of claim 6, wherein the bearing has a plurality of fluid channels extending from the outer surface of the bearing to the inner surface of the bearing.

8. The fluid bearing assembly of claim 7, wherein fluid in the cavity flows through the fluid channels to the inner surface of the bearing.

9. The fluid bearing assembly of claim 1, wherein the housing has a groove to receive the plurality of blades.

10. The fluid bearing assembly of claim 1, wherein the plurality of blades have a rectangular shape.

11. The fluid bearing assembly of claim 1, wherein the fluid includes water, oil, mineral oil, or saline.

12. The fluid bearing assembly of claim 1, wherein the bearing is formed from a polymer.

13. The fluid bearing assembly of claim 1, wherein the bearing is formed from PTFE.

14. The fluid bearing assembly of claim 1, wherein the bearing rotates at speeds between 1,000 rpm and 10,000 rpm.

15. The fluid bearing assembly of claim 1, wherein the bearing rotates at speeds between 10,000 rpm and 100,000 rpm.

16. A fluid bearing assembly for use in laser cutting a stent pattern in tubing, comprising:
    a housing having a gas inlet port and a fluid inlet port;
    a bearing having a plurality of blades and being rotatably mounted within the housing so that the bearing is free to rotate without touching the housing;
    a stent tubing positioned within an inner diameter of the bearing;
    the gas inlet port being positioned to inject pressurized gas on the plurality of blades to impart rotation to the bearing; and
    the fluid inlet port being positioned to inject fluid onto an inner surface of the bearing so that as the bearing rotates, a film of fluid adheres to the inner surface of the bearing and the film of fluid is between the inner surface of the bearing and an outer surface of the stent tubing.

17. The fluid bearing assembly of claim 16, wherein the stent tubing has an outer diameter that is less than an inner diameter of the bearing.

18. The fluid bearing assembly of claim 16, wherein a plurality of gas inlet ports are positioned to inject the pressurized gas on the blades of the bearing.

19. The fluid bearing assembly of claim 18, wherein the gas inlet ports are positioned on an outer surface of the housing and spaced apart in alignment around a circumference of the housing.

20. The fluid bearing assembly of claim 16, wherein a plurality of fluid inlet ports are positioned on an outer surface of the housing.

21. The fluid bearing assembly of claim 20, wherein the plurality of fluid injection ports are spaced apart in alignment around a circumference of the housing.

22. The fluid bearing assembly of claim 16, wherein the fluid injection port is in fluid communication with a cavity formed by an inner surface of the housing and an outer surface of the bearing.

23. The fluid bearing assembly of claim 22, wherein the bearing has a plurality of fluid channels extending from the outer surface of the bearing to the inner surface of the bearing.

24. The fluid bearing assembly of claim 23, wherein fluid in the cavity flows through the fluid channels to the inner surface of the bearing.

25. The fluid bearing assembly of claim 16, wherein the housing has a groove to receive the plurality of blades.

26. The fluid bearing assembly of claim 16, wherein the plurality of blades have a rectangular shape.

27. The fluid bearing assembly of claim 16, wherein the fluid includes water, oil, mineral oil, or saline.

28. The fluid bearing assembly of claim 16, wherein the bearing is formed from a polymer.

29. The fluid bearing assembly of claim 16, wherein the bearing is formed from PTFE.

30. The fluid bearing assembly of claim 16, wherein the bearing rotates at speeds between 1,000 rpm and 10,000 rpm.

31. The fluid bearing assembly of claim 16, wherein the bearing rotates at speeds between 10,000 rpm and 100,000 rpm.

32. A method of supporting a stent tubing for laser cutting a pattern in a stent, comprising:
    providing a computer controlled laser cutting assembly;
    providing a fluid bearing assembly having a bearing within a housing;
    inserting a stent tubing through the fluid bearing assembly and into a collet on the laser cutting assembly;
    simultaneously rotating the bearing in the fluid bearing assembly and injecting a fluid onto an inner surface of the bearing; and
    forming a film of fluid on the inner surface of the bearing so that as the collet rotates and translates the stent tubing the fluid film provides friction reducing barrier between the inner surface of the bearing and an outer surface of the stent tubing.

33. The method of claim 32, wherein the bearing rotates at speeds between 1,000 rpm and 10,000 rpm.

34. The method of claim 32, wherein the bearing rotates at speeds between 10,000 rpm and 100,000 rpm.

* * * * *